United States Patent [19]
Gleich

[11] Patent Number: 5,837,713
[45] Date of Patent: Nov. 17, 1998

[54] TREATMENT OF EOSINOPHIL-ASSOCIATED PATHOLOGIES BY ADMINISTRATION OF TOPICAL ANESTHETICS AND GLUCOCORTICOIDS

[75] Inventor: Gerald J. Gleich, Rochester, Minn.

[73] Assignee: Mayo Foundation for Medical Education and Research, Rochester, Minn.

[21] Appl. No.: 805,623

[22] Filed: Feb. 26, 1997

[51] Int. Cl.$^6$ .................................................. A01N 43/40
[52] U.S. Cl. .......................... 514/312; 514/317; 514/330; 514/535; 514/540; 514/626; 514/826; 514/914
[58] Field of Search ...................... 514/312, 317, 514/330, 535, 540, 626, 826, 914

[56] References Cited

U.S. PATENT DOCUMENTS

| | | |
|---|---|---|
| 4,466,973 | 8/1984 | Rennie .................................... 424/267 |
| 4,626,530 | 12/1986 | Schulte ................................... 514/166 |
| 4,748,022 | 5/1988 | Busciglio ............................. 424/195.1 |
| 5,134,166 | 7/1992 | Bernstein ................................ 514/627 |
| 5,510,339 | 4/1996 | Gleich et al. ............................ 514/171 |
| 5,631,267 | 5/1997 | Gleich et al. ............................ 514/312 |

FOREIGN PATENT DOCUMENTS

94/17790  8/1994  WIPO ............................ A61K 31/00

OTHER PUBLICATIONS

"Merck Manual", 14th Ed., pp. 622–627, (1982).

"Remington's Pharmaceutical Sciences", Mack Publishing Co., Eaton Pennsylvania, pp. 1051–1052, (1985).

Ayars, G.H., et al., "Injurious Effect of the Eosinophil Peroxide–Hydrogen Peoxide–Halide System and Major Basic Protein on Human Nasal Epithelium in vitro", *Am. Rev. Resp. Dis.*, 140, pp. 125–131, (1989).

Barnes, P.J., "Asthma as an Axon Reflex", *The Lancet*, 1, pp. 242–244, (Feb. 1, 1986).

Bascom, R., et al., "Major Basic Protein and Eosinophil–Derived Neurotoxin Concentrations in Nasil–Lavage Fluid After Antigen Challenge: Effect of Systemic Corticosteroids and Relationship to Eosinophil Influx", *J. Allergy Clin. Immunol.*, 84, pp. 338–346, (1989).

Butterfield, J.H., et al., "Chapter 8: Anti–Inflammatory Effect of Glucocorticoids on Eosinophils and Neutrophils", *Anti–Imflammatory Steroid Action: Basic and Clinical Aspects*, Schleimer et al., editors, Academic Press Inc., Schleimer, R.P., et al., (eds.), Academic Press, Inc., San Diego, p. 151–198, (1980).

Chen, W.Y., et al., "Effects of Inhaled Lidocaine on Exercise–Induced Asthma", *Respiration*, 51, 2, pp. 91–97, (1987).

Downes, H., et al., "Lidocaine Aerosols Do Not Prevent Allergic Bronchoconstriction", *Anesth. Anag.*, 60, pp. 28–32, (1981).

Dunnill, M.S., "The Pathology of Asthma, with Special Reference to Changes in the Bronchial Mucosa", *J. Clin. Path.*, 13, pp. 27–33, (1960).

Ellis, A.G., et al., "The Pathological Anatomy of Bronchial Asthma", *Am. J. Med. Sci.*, 136, pp. 407–429, (1908).

Ennight, P.L., et al., "Effect of Lidocaine on the Ventilatory and Airway Response to Exercise in Asthmatics", *Am. Re.. Resp. Disease*, 122, pp. 823–828, (1980).

Filley, W., et al., "Indentification by Immunoflurescence of Eosinophil Granule Major Basic Protein in Lung Tissues of Patents with Broncial Asthma", *The Lancet*, 2, pp. 11–16 (1982).

(List continued on next page.)

Primary Examiner—Terressa Mosley
Attorney, Agent, or Firm—Schwegman, Lundberg, Woessner & Kluth, P.A.

[57] ABSTRACT

A therapeutic method is provided to treat an eosinophil-associated pathology, such as bronchial asthma, by administering to a mammal in need of such treatment, an effective amount of at least one topical anesthetic, such as lidocaine, with an effective amount of one or more glucocorticoids, or the pharmaceutically acceptable salts thereof.

23 Claims, 5 Drawing Sheets

OTHER PUBLICATIONS

Frigas, E., et al., "Cytotoxic Effects of the Guinea Pig Eosinophil Major Basic Protein on Tracheal Epithelium", *Lab. Invest.*, 42, 35–43 (1980).

Frigas, E., et al., "Elevated Levels of the Eosinohil: Granule Major Basic Protein in the Sputum of Patents with Bronchial Asthma", *Mayo Clinic. Proc.* 56, pp. 345–353, (1981).

Fujisawa, T., et al., "Regulatory Effects of Cytokines on Eosinohil Degranulation", *J. Immunol.*, 144, pp. 642–646, (1990).

Gleich, G.J., "Cytoxic Properties of the Esinophil Major Basic Protein", *J. Immunol.*, 123, pp. 2925–2927, (1979).

Gleich, G.J., "Identification of a Major Basic Protein in Guinea Pig Eosinophil Granules", *J. Exp. Med.*, 137, pp. 1459–1471, (1973).

Gleich, G.J., et al., "The Eosinophilic Leukocyte: Structure and Function", *Adv. Immunol.*, 39, pp. 177–253 (1986).

Gross, N.J., et al., "Chapter 34: Anticholinergic Drugs", *Allergy, Principles and Practice*, vol. 1, E. Middleton Jr. et al., (ed.) The C.V. Mosby Company, pp. 782–808, (1988).

Gundel, R.H., et al., "Repeated Antigen Inhalation Results in a Prolonged Airway Eosinophilia and Airway Hyperresponsiveness in Primates", *J. Appl. Physiol.*, 68, pp. 779–786 (1990).

Hamid, Q., et al., "Expression of mRNA for Interleukin-5 in Mucosal Bronchial Biopsies from Asthma", *J. Clin. Invest.*, 87, pp. 1541–1546 (1991).

Harlin, S.L., et al., "A Clinical and Pathologic Study of Chronic Sinusitis: The Role of the Eosinophil", *J. Allergy Clin. Immunol.*, 81, pp. 867–875 (1988).

Hastie, A.T., et al., "The Effect of Purified Human Ecsinophil Major Basic Protein on Mammalian Ciliary Activity", *Am. Rev. Resp. Dis.*, 135, pp. 845–853 (1987).

Horn, B.R., et al., "Total Eosinophil Counts in the Management of Bronchial Asthma", *N. Engl. J. Med.*, 292, pp. 1152–1155 (1975).

Krasnowska, M., et al., Translation of "A Test of Lidocaine Usage in the Treatment of Bronchial Asthma", *Pneum. Pol.*, 50, 269–273 (1982).

Lamas, A.M., et al., "Glucocorticoids Specifically Decrease Eosinophil Survival", *J. Allergy Clin. Immunol.*, 85, Abstract No. 554, p. 282, (1990).

Lamas, A.M., et al., "Human Endothelial Cells Prolong Eosinophil Survival", *J. Immunol.*, 142, pp. 3978–3984, (1989).

Mauser, P.J., et al., "The Effect of Anti-Il-5 on Antigen-Induce Airway Hyperreactivity and Pulmonary Eosinophilia in Guinea Pigs", *Am. Rev. Respir. Dis.*, 145, p. A8, (1992).

Motojima, S., et al., "Toxicity of Eosinophil Cationic Proteins for Guinea Pig Tracheal Epithelium in Vitro", *Am. Rev. Resir. Dis.*, 139, pp. 801–805, (1989).

Rothenberg, M.E., et al., "Human Eosinophil have Prolonged Survival, Enhanced Functional Properties, and Become Hypodense when Exposed to Human Interleukin 3", *J. Clin. Invest.*, 81, pp. 1986–1992, (1988).

Schleimer, R.P., et al., "Effects of Glucocorticosteroids on Inflammatory Cells Relevant to Their Therapuetic Applications in Asthma", *Am. Rev. Respir., Dis.*, 141, pp. S59–S69, (1990).

Sedgwich, J.B., et al., "Immediate and Late Airway Response of Allergic Rhinitis Patients to Segmental Antigen Challenge", *Am. Rev. Respir. Dis.*, vol. 144, No. 6, pp. 1274–1281, (1991).

Sehmi, R., et al., "Interleukin-5 Selectively Enhances the Chemotatics Response to Eosinophils Obtained from Normal but not Eosinophilic Subjects", *Blood*, 79, pp. 2952–2959, (1992).

Silberstein, D.S., et al., "Enhancement of Human Eosinophil Cytoxicity and Leukotriene Synthesis by Biosynthetic (Recombinant) Granulocyte–Macrophage Colony–Stimulating Factor", *J. Immunol.*, 137, pp. 3290–3294, (1986).

Silberstein, D.S., et al., "Hemopoietins for Eosinophils", *Hematol. Oncol. Clin. North Am.*, 3, pp. 511–513, (1989).

Trocme, S.D., et al., "Conjunctival Deposition of Eosinophil Granule Major Basic Protein in Vernal Keratoconjunctivitis and Contact Lens–Associated Giant Papillary Conjuctivitis", *Am. J. Ophthamol.*, 108, pp. 57–63, (1989).

Tullett, W.M., "Effect of Lignocaine, Sodium Cromoglycate, and Ipratropium Bromide in Exercise-induced Asthma", *Thorax*, 37, pp. 737–740, (1982).

Udell, I.J., et al., "Eosinophil Granule Major Basic and Protein and Charot–Leyden Crystal Protein in Human Tears", *Am. J. Opthamol.*, 92, pp. 824–828, (1981).

Valerius, T., et al., "Effects of IFN on Human Eosinophils in Comparison with Other Cytokines", *J. Immunol*, 145, pp. 2950–2958, (1990).

Wallen, N., et al., "Glucocorticoids Inhibit Cytokine–Mediated Eosinohpil Survival", *J. Immunol.*, 147, pp. 3490–3495, (1991).

Wardlaw, A.J., et al., "Eposinophils and Mast Cells in Bronchoalveolar Lavage in Subjects with Mild Asthma", *Am. Rev. Resp. Dis.*, 137, pp. 62–69, (1988).

Wasmoen, T.L., et al., "Biochemical and Amino Acid Sequence Analysis of Human Eosinophil Granule Major Basic Protein", *J. Biol. Chem.*, 263, pp. 2559–12563, (1988).

TREATMENT OF EOSINOPHIL-ASSOCIATED PATHOLOGIES BY ADMINISTRATION OF TOPICAL ANESTHETICS AND GLUCOCORTICOIDS

GOVERNMENTAL RIGHTS

This invention was made with the assistance of the United States Public Health Service under grant number AI-15231. The U.S. Government has certain rights in the invention.

BACKGROUND OF THE INVENTION

For many years, bronchial asthma was regarded as an abnormality of respiratory smooth muscle in which afflicted individuals experience the onset of bronchospasm as a consequence of overactivity of the bronchial smooth muscle. Later, the bronchial mast cell was thought to play a critical role in the stimulation of bronchial smooth muscle by producing leukotriene C4 (the slow-reacting substance of anaphylaxis) and histamine, which cause contraction. However, over the past few years, a dramatic change in thinking regarding the pathophysiology of bronchial asthma has occurred and the involvement of eosinophilic leukocytes, or "eosinophils", in the inflammation of the airway has been suspected.

Eosinophils are a type of leukocyte containing cytoplasmic granules that stain strongly with acidic dyes. Eosinophils have been associated with bronchial asthma since the early part of this century and they are characteristically found in large numbers in the lung tissue of patients dying of asthma (Ellis et al., *J. Med. Sci.*, 136, 407 (1908)). In the mid 1970's, it was demonstrated that the severity of bronchial asthma can be related to the number of eosinophils in the peripheral blood of the patients (Horn et al., *N. Engl. J. Med.*, 292 1152 (1975)).

Also around this time, studies of eosinophils had shown the presence of basic (cationic) granule proteins. One of the principal proteins associated with eosinophil granules, the major basic protein (MBP), was so-named because, in the guinea pig it comprises more than 50% the granule protein, is strongly basic (arginine-rich), and is proteinaceous (Gleich, *J. Exp. Med.*, 137, 1459 (1973); Wasmoen et al., *J. Biol. Chem.*, 263, 12559 (1988)). MBP is toxic to worms (helminths) and mammalian cells, and causes damage to bronchial respiratory epithelium (Gleich et al., *Adv. Immunol.*, 39, 177 (1986)).

For example, direct application of MBP to respiratory epithelium in concentrations as low as 10 μg/ml ($7.1 \times 10^{-7}$M) causes ciliostasis and epithelial damage. This damage consists of desquamation of epithelial cells into the lumen of the respiratory tract, as well as frank disruption of epithelial cells. The effects of MBP are dose-related and higher doses cause damage more quickly and to a greater extent than lower doses (Frigas et al., *Lab. Invest.*, 42, 35 (1980)). These effects are caused both by MBP from guinea pig eosinophils and from human eosinophils, and impact both guinea pig and human respiratory tissues (Gleich et al., *J. Immunol.*, 123, 2925 (1979); Frigas et al., *Mayo Clin. Proc.*, 56, 345 (1981)).

The ciliostasis, desquamation of respiratory epithelial cells, and damage to the respiratory epithelial cells caused by MBP are suggestive of the pathologic changes observed in bronchial asthma. In bronchial asthma an exudate of eosinophils, normal and degenerating bronchial epithelial cells, and clumps of epithelial cells, referred to as Creola bodies, are present in the bronchial lumen. In the bronchial mucosa and submucosa, edema, separation and shedding of ciliated cells, and eosinophil infiltration are seen. Thus, the effects of the eosinophil granule MBP in vitro are similar to the pathology characteristic of bronchial asthma (Dunnill, *J. Clin. Path.*, 13, 27 (1960)).

Because of this discovery, the levels of MBP in sputum of patients with bronchial asthma were measured to determine whether they were elevated and to what degree. Levels of MBP in sputum samples from 206 patients with various respiratory diseases were measured by radioimmunoassay. In 165 of these patients, MBP was not measurable or the concentrations of MBP were less than 0.1 μg/ml. In these 165 patients, only one patient carried the diagnosis of asthma. Among 41 patients with sputum concentrations of MBP greater than 0.1 μg/ml, 28 were diagnosed as having asthma and in the remaining 13 patients, six had obstructive lung disease which is often confused with asthma. In 15 patients hospitalized for treatment of asthma, sputum MBP levels ranged from 0.5 ($0.04 \times 10^{-6}$M) to 93 μg/ml ($6.6 \times 10^{-6}$M) (geometric mean 7.1 μg/ml, $0.51 \times 10^{-6}$M). Further, the levels of sputum MBP in these 15 patients declined during therapy with glucocorticoids (Frigas et al., *Mayo Clinic. Proc.*, 56, 345 (1981)). These results indicated that MBP levels in the toxic range were present in the sputum of patients with asthma, that levels of sputum MBP were highest in acutely ill patients, and that sputum MBP levels decline after steroid therapy.

The possibility that MBP directly causes damage to bronchial epithelium was tested utilizing immunofluorescence localization of MBP in lung tissues of patients dying of asthma (Filley et al., *Lancet*, 2, 11 (1982)). Patients dying of asthma had the classical pathologic features of bronchial asthma, including a thickened basement membrane zone, goblet cell hyperplasia, and peribronchial inflammation, infiltrates with eosinophils in the lamina propria. Examination of these same sections by immunofluorescence to localize MBP, revealed MBP deposition onto damaged bronchial epithelium. These results demonstrate that MBP was released from the eosinophil and was present in tissues at the site of damage.

Subsequent studies extended these observations showing that not only MBP, but two of the other cationic eosinophil granule proteins, namely eosinophil peroxidase (EPO) and eosinophil cationic protein (ECP), have the capacity to damage bronchial epithelium (Motojima et al., *Am. Rev. Respir. Dis.*, 139, 801 (1989)). Analyses of the effect of MBP on respiratory epithelium showed that although MBP reduced the frequency of ciliary beating, its predominant effect was to reduce the number of beating ciliated cells. The effect of MBP in causing cessation of ciliary beating was seen in respiratory epithelial cells in the epithelium itself as well as in axonemes (the contractile elements of the cilia) (Hastie et al., *Am. Rev. Resp. Dis.*, 135, 845 (1987)).

One of the signal abnormalities in bronchial asthma is bronchial hyperactivity. Bronchial hyperactivity is manifested in patients as a marked irritability of the respiratory tract to nonspecific stimuli including cold air, dust, and, in the laboratory, to inhaled methacholine. Indeed, this hyperactivity is a diagnostic criterion for asthma (N. J. Gross et al., in *Allergy, Principles and Practice*, Vol. I., 4 Middleton, Jr. et al., eds. (1988) at page 790). Analyses of MBP in the lung secretions of patients with asthma (obtained by lavage of the bronchi and alveoli) showed that MBP levels in lung fluids are correlated with bronchial hyperactivity (Wardlaw et al., *Am. Rev. Resp. Dis.*, 137, 62 (1988)). In cynomolgus monkeys, provocation of inflammation rich in eosinophils was associated with an increase in bronchial hyperactivity and with the presence of MBP in lung secretion; both the numbers of eosinophils and the MBP concentration were significantly correlated with bronchial hyperactivity to methacholine (Gundel et al., *J. Appl. Physiol.,* 68, 779 (1990)).

At the molecular level, eosinophil proliferation and differentiation are regulated by various cytokines, such as IL-3, IL-5 and GM-CSF. See Silberstein et al., *Hematol. Oncol. Clin. North Am.,* 3, 511 (1989). These cytokines, as well as IFN-γ, have been shown to prolong survival of eosinophils in vitro by Valerius et al., *J. Immunol.,* 145, 2950 (1990), and to augment eosinophil function (Rothenberg et al., *J. Clin. Invest.,* 81 1986 (1988); Fujisawa et al., *J. Immunol.,* 144, 642 (1990); Silberstein et al., *J. Immunol.,* 137, 3290 (1986)). Furthermore, IL-5 primes eosinophils for enhanced locomotor responses to chemotactic agents, such as platelet-activating factor, leukotriene B4, and IL-8 (Sehmi et al., *Blood,* 79, 2952 (1992)). Also, recent information indicates that IL-5 is present in the lung following allergen-induced pulmonary late allergic reactions (Sedgwick et al., *Am. Rev. Respir. Dis.,* 144, 1274 (1991)) and mRNA for IL-5 is expressed in the bronchial epithelium of patients with asthma (Hamid et al., *J. Clin. Invest.,* 87, 1541 (1991)). These observations suggest that the inflammation associated with asthma is critically dependent on the presence of cytokines, especially IL-5, and recent data showing that antibodies to IL-5 block both antigen-induced eosinophilia and antigen-induced bronchial hyperactivity support that view (Mauser et al., *Am. J. v. Respir. Dis.,* 145, A859 (1992)).

Glucocorticoids are the most useful class of drugs for treating many eosinophil-related disorders, including bronchial asthma (Schleimer et al., *Am. Rev. Respir. Dis.,* 141, 559 (1990)). They produce eosinopenia in normal persons, decrease circulating eosinophils in patients with eosinophilia, and reduce eosinophil influx at inflammatory sites (Butterfield et al., in *Antiinflammatory Steroid Action: Basic and Clinical Aspects,* Schleimer et al., eds. Academic Press, Inc. (1989) at p. 151. The mechanism of these effects is still uncertain. Lamas et al. in *J. Immunol.,* 142, 3978 (1989) and *J. Allergy Clin. Immunol.,* 85, 282 (1990) have reported that supernatants from human vascular endothelial cells cultured with glucocorticoids had reduced eosinophil survival-enhancing activity in vitro.

Recently, Wallen et al., *J. Immunol.,* 147, 3940 (1991) reported the dose-dependent inhibition of IL-5-mediated eosinophil survival by dexamethasone, methylprednisolone and hydrocortisone, and the inhibition of IL-3-, GM-CSF-, and IFN-γ-mediated eosinophil survival by dexamethasone. Dexamethasone produced a dose-dependent increase in the $EC_{50}$ for IL-5-mediated viability enhancement. The relative eosinophil viability inhibitory potencies of the glucocorticoids tested correlated with previously described antiinflammatory potencies and with the affinities for the glucocorticoid receptor: dexamethasone>methylprednisolone>hydrocortisone.

For many patients with asthma, glucocorticoids are the principal therapy and these patients may require glucocorticoid therapy for long periods of time, e.g., months to years. In fact, the disease can be characterized as one of chronic glucocorticoid toxicity, in that the toxicity of these steroids can cause severe morbidity and even mortality in the patients. Furthermore, cessation of glucocorticoid therapy leads to withdrawal symptoms, such as malaise and muscle pain. However, presently glucocorticoids are the only effective therapy for severe asthma, and are prescribed long-term despite their toxicity.

The information discussed above pertains to bronchial asthma and the role of toxic eosinophil granule proteins exemplified by MBP in the pathophysiology of bronchial asthma. Evidence exists that these toxic proteins also contribute to the pathogenesis of diseases associated with eosinophil infiltration in the upper respiratory tract. For example, Ayars et al. in *Am. Rev. Resp. Dis.,* 140, 125 (1989), have reported that MBP is toxic to respiratory epithelium from the nose, and Bascom et al., in *J. Allergy Clin. Immunol.,* 84, 338 (1989) found that elevated MBP concentrations are present in nasal fluids following experimental hay fever. As reported by Harlin et al., *J. Allergy Clin. Immunol.,* 81, 867 (1988), MBP is deposited on respiratory epithelium of the upper airway in association with damage to the epithelium. Therefore, toxic eosinophil granule proteins may cause disease of the upper airway in the same manner as they likely do in the lower airway in the case of bronchial asthma.

Finally, Udell et al., in *Am. J. Ophthamol.* 92, 824 (1981) reported that MBP is elevated in tears of patients with vernal conjunctivitis, a form of allergic inflammation of the eye, and Trocme et al., in *Am. J. Ophthamol,* 108, 57 (1989) found that MBP is deposited into inflamed conjunctiva of such patients. Thus, evidence exists that MBP may act as a toxin to the conjunctiva.

Therefore, a need exists for improved therapeutic methods to treat pathologies, such as bronchial asthma, which are caused by, or aggravated by, eosinophils or the toxic proteins released by eosinophils.

SUMMARY OF THE INVENTION

The present invention provides a method for treating a pathology characterized by elevated levels of eosinophils (i.e., an eosinophil-associated pathology) comprising co-administering to a mammal in need of such treatment an amount of a topical anesthetic and an amount of a glucocorticoid, wherein said amounts are effective to counteract at least one of the symptoms of said pathology. It is preferred that the mammal be a human, such as a patient afflicted with bronchial asthma.

As used herein, the terms "co-administer" or "co-administration" are defined to encompass administration simultaneously, as in admixture in a single composition, or sequentially, so that they are delivered to, and present at, the target site in vivo, together in therapeutically effective amounts.

Gleich et al. (U.S. Pat. No. 5,510,339) discloses the use of topical anesthetics to reduce dependence of asthma patients on steroid therapy. In contrast, the present invention is based on Applicant's surprising discovery that lidocaine and dexamethasone act synergistically to inhibit human eosinophil survival in vitro. That is, the administration of a combination of a topical anesthetic and a glucocorticoid requires less of either agent for therapeutic efficacy than would be expected to be required on the basis of an additive effect. Thus, the treatment of eosinophil-associated diseases with a combination of topical anesthetics and glucocorticoids is more effective than treatment with either agent alone.

A preferred embodiment of the present method is directed to a therapy for bronchial asthma, eosinophil-associated intranasal inflammation, including nasal polyps, inflammation of the paranasal sinuses and allergic rhinitis, eosinophil-associated cutaneous inflammation, eosinophil-associated disorders of the gastrointestinal tract, such as inflammatory bowel disease, and eosinophil-associated inflammation of the eye, such as vernal and allergic conjunctivitis. For example, the present invention provides a therapy for bronchial asthma and the other hypersensitivity diseases of the respiratory tract, by topical administration, e.g., by inhalation or insufflation, of a composition comprising a topical anesthetic, such as lidocaine, bupiracaine, etidocaine, tetracaine and the like, and a glucocorticoid. The topical anesthetic in turn is able to inhibit the activity of eosinophil-active cytokines, such as IL-5, and thus, to limit the negative effects of eosinophils on respiratory epithelium or other tissue. The activity of the topical anesthetic is effectively enhanced by the co-administration of the glucocorticoid. Topical administration of the composition of the present invention, e.g., in nose drops or eye drops, can relieve the symptoms or conditions due to eosinophil-associated inflammation of the nasal passages or of the eye, such as allergic rhinitis or allergic conjunctivitis.

As used herein, the term topical anesthetic or glucocorticoid encompasses the free compounds, as well as the pharmaceutically acceptable salts thereof.

DETAILED DESCRIPTION OF THE INVENTION

Eosinophil-Associated Pathologies

Figure 1:
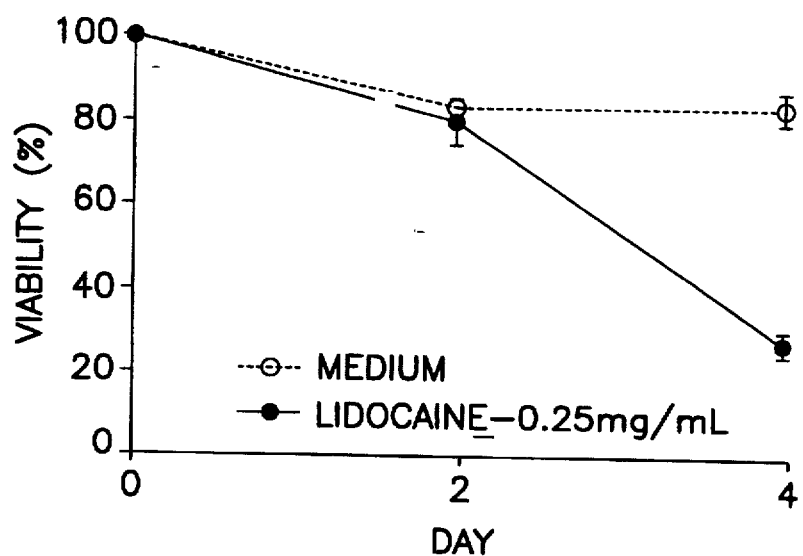
FIG. 1 is a graphical depiction of the time course of eosinophil viability inhibition effect by lidocaine. Culture medium was supplemented with recombinant human interleukin 5 (rhIL-5), 10 pg/ml, and the effects on eosinophil viability of lidocaine (0.25 mg/ml)(·), or medium control (Hybri-Care®) (American Type Culture Collection, Rockville, Md.) containing gentamicin, 50 µg/ml and 10% defined calf serum (Hyclone Laboratories, Logan, Utah) were tested by comparing viabilities at two and four days.

In addition to the hypersensitivity diseases discussed above, such as bronchial asthma, nasal inflammation and conjunctivitis, many other conditions associated with elevated levels of eosinophil activation and accumulation, some of which are presently treated with glucocorticoids, are amenable to treatment by the present combination therapy. These conditions include, but are not limited to, chronic eosinophilic pneumonia, allergic rhinitis, allergic sinusitis, allergic gastroenteropathy, eosinophilic gastroenteritis, atopic dermatitis, bullous pemphigoid, episodic angiodema associated with eosinophilia, ulcerative colitis, inflammatory bowel disease, vernal conjunctivitis, giant papillary conjunctivitis, and allergic conjunctivitis.

Topical Anesthetics

Topical anesthetics, all of which are believed to be useful in the present invention, are an art-recognized class of drugs which temporarily interrupt mammalian nerve transmissions. They can generally be grouped into two chemical classifications structurally: the N-arylamides or carboxamides, such as lidocaine; and the aminoalkylbenzoates, such as procaine, benoxinate and proparacaine. Preferred N-arylamides comprise the N—($C_7$–$C_{22}$)arylamides of amino-substituted ($C_1$–$C_5$) carboxylic acids, e.g., N-[(mono or di-($C_1$–$C_4$)alkyl)phenyl] amides of aliphatic ($C_1$–$C_5$)carboxylic acids, which acids are preferably substituted with the moiety (R)($R^1$)N— wherein R is H or ($C_1$–$C_5$)alkyl and $R^1$ is ($C_1$–$C_5$)alkyl. For example, a preferred carboxylic acid can have the general formula (R)($R^1$)N(X)$CO_2$H where R and $R^1$ are as defined above and X is a branched- or straight-chain ($C_1$–$C_5$) alkylene group such as 1,1-ethylene, 1,2-ethylene, methylene, 2,2-propylene, 1,3-propylene, and the like. Another preferred class of N-arylamides are the N-[(mono- or di- ($C_1$–$C_4$) alkyl) phenyl]amides of 5- or 6-membered-heterocycloaliphatic carboxylic acids, which acids comprise one or two [($C_1$–$C_4$)alkyl-substituted]N atoms, i.e., N-butylpiperidine-2-carboxylic acid.

The aminoalkylbenzoates include esters between benzoic acids and alcohols of the general formula ($R^4$)($R^5$)N(X)OH, wherein X is as defined above, $R^4$ is H or ($C_1$–$C_4$)-alkyl, $R^5$ is ($C_1$–$C_4$)alkyl or $R^4$ and $R^5$ taken together with N are a 5- or 6-membered heterocycloaliphatic ring, optionally substituted by ($C_1$–$C_3$)alkyl or comprising an additional ring O- or N-atom. The benzoic acid moiety can be the moiety ($R^2$)($R^3$) Ar$CO_2$H wherein Ar is an aromatic —$C_6H_3$— radical "phenylene" and (phenylene) and each $R^2$ and $R^3$ is H, halo, preferably Cl, ($R^5$)(H)N—, $H_2$N— or ($C_1$–$C_5$) alkoxy.

Useful topical anesthetics include lidocaine ((2-diethylamino)-N-(2,6-dimethylphenyl)-acetamide) (see Lofgren et al. (U.S. Pat. No. 2,441,498), May & Baker (British Patent No. 706409) and Macfarlane & Co. (British Patent No. 758,224)); bupivacaine (1-butyl-N-(2,6-dimethylphenyl)-2-piperidinecarboxyamide) (see Thuresson et al., (U.S. Pat. Nos. 1,166,802 and 1,180,712)); mepivacaine (2-piperidinecarboxyamide, N-(2,6-dimethylphenyl)-1-methyl), chloroprocaine (4-amino-2-chlorobenzoic acid 2-(diethylamino)ethyl ester); procaine;4-aminobenzoic acid 2-(diethylamino)ethyl ester); etidocaine (N-(2,6-dimethylphenyl)-2-(ethylpropylamino)butanamide; see, Astra (German Patent No. 2162744)); tetracaine (4-(butylamino)benzoic acid 2-(dimethylaminoethyl ester; see Shupe (U.S. Pat. No. 3,272,700)); benoxinate (4-amino-3-butoxybenzoic acid 2-(diethylamino)ethyl ester (U.K. Patent No. 654,484)) proparacaine (3-amino-4-propoxybenzoic acid 2-(diethylamino) ethyl ester); dibucaine (3-butoxy-N-[2-(diethylamino)ethyl]-4-quinolinecarboxyamide; Miescher (U.S. Pat. No. 1,825,623)); dyclonine (1-(4-butoxyphenyl)-3-(1-piperidinyl-1-propanone)); isobucaine (1-propanol, 2-methyl-2-[(2-methylpropyl)amino]benzoate; meprylcaine ([(2-methyl)(2-propylamino)propyl]benzoate); piperocaine ((2-methylpiperidin-1-ylpropyl(benzoate)); prilocaine (N-(2-methylphenyl)-2 -(propylamino) propanamide); propoxycaine (2-(diethylamino)ethyl-([2'-methyl-4-amino]benzoate)); pyrrocaine (1-(pyrrolidin-1-yl) -N-(2,6-dimethylphenyl)acetamide, butacaine (((3-dibutylamino)propyl)-(2'-aminobenzoate)); cyclomethylcaine (((3-(2'-methylproperidine-n yl))propyl)-[4'-cyclohexyloxy-benzoate]); dimethyisoquin, diperodon, hexylcaine ((([(2-cyclohexylamino)(1-methyl)]ethyl) (benzoate); proparacaine (((2-diethylamino)ethyl) [(4'-propyloxyl-3'-amino)benzoate]); cocaine and its analogs (see, Carroll et al., J. Med. Chem., 34, 2719 (1991); Eur. J.

*Pharmacol.*, 184, 329 (1990); and the pharmaceutically acceptable salts thereof.

Preferred salts include the amine addition salts of inorganic and organic acids, e.g., the hydrochloride, hydrobromide, sulfate, oxalate, fumarate, citrate, malate, propionate and phosphate salts. The hydrochloride and sulfate salts are preferred for use in the present invention.

These topical anesthetics and the salts thereof are discussed in detail in *Remington's Pharmaceutical Sciences*, A. Osol, ed., Mack Pub. Co., Easton, Pa. (16th ed. 1980), and in *The Merck Index* (11th ed. 1989).

Glucocorticoids

Over 50 steroids have been shown to be present in the adrenal cortex. Only seven of these, however, have been shown to exert a significant biological effect related to adrenal cortical function. However, the adrenal cortex also produces androgenic steroids. All of the adrenal cortical steroids, except the androgens, contain 21 carbon atoms, an α, β-unsaturated ketone in ring A, and an α-ketol chain attached to ring D. They differ in extent of oxygenation or hydroxylation at carbons 11, 17, or 19.

Depending on whether the predominant biological effect is related to electrolyte and water metabolism, or to carbohydrate and protein metabolism, the cortical steroids are classified as either mineralcorticoid or glucocorticoid, respectively. In general, clinical experience has indicated that the anti-inflammatory activity of adrenal cortical steroids in man correlates well with their glucocorticoid activity. The undesirable side effects (sodium retention, edema) are associated with mineralcorticoid activity.

Interest in glucocorticoids primarily focuses on their anti-inflammatory and immunosuppressant effects. Although the administration of glucocorticoids for their antiinflammatory effects is palliative therapy because the underlying cause of the disease remains, the suppression of inflammation and its consequences has made these agents of great value clinically—indeed, at times lifesaving. The glucocorticoids are also of immense value in treating diseases that result from undesirable immune reactions. These diseases range from conditions that are predominantly the consequence of humoral immunity, such as idiopathic thrombocytopenia, to those that are mediated by cellular immune mechanisms, such as the rejection of transplanted organs. The immunosuppressive and antiinflammatory actions of the glucocorticoids are inextricably linked because they both result in large part from inhibition of specific function of leukocytes. In several instances these effects on leukocytes are a consequence of glucocorticoid-induced inhibition of the elaboration and/or action of lymphokines.

Glucocorticoids useful in the practice of the present invention include, but are not limited to, beclomethasone dipropionate, betamethasone, betamethasone acetate, betamethasone sodium phosphate, betamethasone valerate, budesonide, cortisol, cortisol acetate, cortisol cypionate, cortisol sodium phosphate, cortisol sodium succinate, cortisone acetate, dexamethasone, flumethasone pivalate, fluocinolone acetonide, fluocinonide, fluorometholone, flurandrenolide, fluticasone, meprednisone, methylprednisolone, methylprednisolone acetate, methylprednisolone sodium succinate, paramethasone acetate, prednisolone, prednisolone acetate, prednisolone sodium phosphate, prednisolone sodium succinate, prednisolone succinate, prednisolone tebutate, triamcinolone, triamcinolone acetonide, triamcinolone diacetate, triamcinolone hexacetonide, amcinonide, betamethasone benzoate, betamethasone dipropionate, clobetasone butyrate, clocortolone pivalate, cortisol butyrate, cortisol valerate, desonide, desoximetasone, and the like. These glucocorticoids and the salts thereof are discussed in detail in *Remington's Pharmaceutical Sciences*, A. Osol, ed., Mack Pub. Co., Easton, Pa. (16th ed. 1980).

Preferably, the glucocorticoid is beclomethasone, betamethasone, budesonide, cortisol, cortisone, dexamethasone, flumethasone, fluocinolone, fluocinonide, fluorometholone, flurandrenolide, fluticasone, meprednisone, methylprednisolone, prednisolone, triamcinolone, amcinonide, desonide, desoximetasone, or a pharmaceutically acceptable salt thereof. More preferably the glucocorticoid is betamethasone, cortisol, cortisone, dexamethasone, meprednisone, methylprednisolone, or prednisolone or a pharmaceutically acceptable salt thereof. Most preferably, the glucocorticoid is dexamethasone or a pharmaceutically acceptable salt thereof. For example, dexamethasone salts useful in the practice of the present method include the tert-butylacetate, the 21-phosphate, 21-phosphate disodium salt, the tetrahydrophthalate, the 21-palmitate, the 17,21-dipropionate, the 21-isonicotinate, and the 21-diethyl-amino-acetate salts of dexamethasone.

Administration and Dosages

The topical anesthetic or anesthetics and the glucocorticoid or glucocorticoids (the "active ingredients") are co-administered so that they are both present at the active site (in vivo) in therapeutically effective amounts. Thus, the active ingredients may be combined either in the pure form or in combination with one or more pharmaceutically acceptable carriers in a single composition. Alternatively, the active ingredients can be formulated as discrete compositions and administered concurrently, i.e., via a double lumen catheter, as encapsulated coated microparticles, via an inhaler with double outlets, or via like dosage forms. The active ingredients may also be administered sequentially, i.e., via the use of two discrete inhalers, injections, tablets or the like, administered so that the active ingredients both reach therapeutic levels together at the target site.

For example, the active ingredients may be administered as a single composition suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The active ingredients may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Furthermore, compositions suitable for oral administration may be presented as discrete unit dosage forms such as hard or soft gelatin capsules, cachets or tablets each containing a predetermined amount of the active ingredients; as a powder or as granules; as a solution, a suspension or as an emulsion; or in a chewable base such as a synthetic resin for ingestion of the active ingredients from a chewing gum. The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The active ingredients may also be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

For topical administration to the epidermis, the active ingredients may be formulated as ointments, creams or lotions, or as the active ingredients of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842.

When desired, the above-described formulations can be adapted to give sustained release of the active ingredients employed, e.g., by combination with certain hydrophilic polymer matrices, e.g., comprising natural gels, synthetic polymer gels or mixtures thereof.

Compositions suitable for rectal administration wherein the carrier is a solid are most preferably presented as unit dose suppositories. Suitable carriers include cocoa butter and other materials commonly used in the art, and the suppositories may be conveniently formed by admixture of the active compounds with the softened or melted carrier(s) followed by chilling and shaping in molds.

Compositions suitable for vaginal administration may be presented as pessaries, tampons, creams, gels, pastes, foams or sprays containing, in addition to the active ingredients, such carriers as are known in the art to be appropriate.

The active ingredients may also be formulated so as to be suitable for administration by inhalation or insufflation or for nasal, intraocular or other topical (including buccal and sub-lingual) administration. For example, for administration to the upper (nasal) or lower respiratory tract by inhalation, the active ingredients are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the active ingredients may take the form of a dry powder composition, for example, a powder mix of the active ingredients and a suitable powder base such as lactose or starch. The powder composition may be presented in unit dosage form in, for example, capsules or cartridges or, e.g., gelatin or blister packs from which the powder may be administered with the aid of an inhalate insufflator or a metered-dose inhaler.

For intra-nasal administration, the active ingredients may also be administered via nose drops, a liquid spray, such as via a plastic bottle atomizer or metered-dose inhaler. Typical of atomizers are the Mistometer® (Wintrop) and the Medihaler® (Riker).

Drops, such as eye drops, or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The active ingredients may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as antimicrobial agents, or preservatives. Furthermore, the active ingredients may, also be used in combination with other therapeutic agents, for example, bronchodilators.

It will be further appreciated that the amount of a formulation comprising the active ingredients required for use in treatment will vary not only with the particular topical anesthetic and glucocorticoid selected, but also with the route of administration, the nature of the condition being treated and the age and condition of the patient and will be ultimately at the discretion of the attendant physician or veterinarian. In general, however, a suitable unit dose of topical anesthetic for counteracting respiratory tract symptomatology will deliver from about 0.05 to about 10–15 mg/kg, e.g., from about 0.10 to about 5.0 mg/kg of body weight per day. A suitable unit dose of glucocorticoid will deliver from about 0.050 to about 10–15 mg/kg, e.g., from about 0.10 to about 5.0 mg/kg of body weight per day.

The desired dose may conveniently be presented in a single dose or as divided doses administered at appropriate intervals, for example, as two, three, four or more sub-doses per day. The sub-dose itself may be further divided, e.g., into a number of discrete, loosely spaced administrations such as multiple inhalations from an insufflator or by application of a plurality of drops into the eye or nose.

The invention will be further described by reference to the following detailed Examples.

EXAMPLE 1

Inhibition of IL-5-Mediated Eosinophil Survival by Lidocaine

A. Eosinophil Purification

Eosinophils were purified from human peripheral blood, as previously described by Fujisawa et al., *J. Immunol.*, 144, 642 (1990). Briefly, heparinized (10 U/ml) venous blood was obtained from normal volunteers or patients with mild asthma or hay fever and sedimented with 6% dextran in 0.9% NaCl (Gentran 70) (Travenol Laboratories, Deerfield, Ill.) at 5:1 (v/v) ratio for 45 minutes at 37° C. The buffer coat was collected and washed twice in Pipes buffer (25 mM piperazine-N,N'-bis[2-ethanesulfonic acid], 110 mM NaCl, 5 mM KCL, 25 mM NaOH, 5.4 mM glucose, pH 7.4) with 50 U/ml DNase (Sigma Chemical Co., St. Louis, Mo.). The cells were suspended in 2.4 ml of Percoll (Sigma), density 1.070 g/ml, with 5% heat-inactivated defined calf serum (DCS) (Hyclone Laboratories, Logan, Utah) and overlayered on a discontinuous Percoll gradient consisting of the following densities (g/ml): 1.080, 1.085, 1.090, 1.100, and 1.120. The osmolarity of Percoll ranged from 290 to 315 mOsm/kg and the pH was 7.4. Cells were centrifuged through the gradient at 1,000 g in a JA-20 fixed angle rotor on a Beckman J2-21 centrifuge at 4° C. for 45 minutes. Fractions were collected and eosinophil numbers were determined utilizing Randolph's stain. Eosinophil-rich fractions were pooled, washed twice in Pipes buffer with 1% DCS, and used for experiments immediately. The eosinophil preparations were >80% pure and >98% viable, as determined by Randolph's stain and by trypan blue exclusion, respectively. The contaminating cells were neutrophils. There was no contamination by lymphocytes or monocytes.

B. Eosinophil-Survival Assay

Eosinophils were cultured at 37° C. and 5% $CO_2$ in 200 µl Hydri-Care® medium containing gentamicin and 10% DCS in 90-well, flat-bottom tissue culture plates at a concentration of $2.5\times10^5$/ml or $1.25\times10^5$ cells/ml. No difference in viability was observed at these two cell concentrations. Viability was determined at day 4 for all experiments unless otherwise specified. A Neubauer hemacytometer (C. A. Hausser & Son; Philadelphia, Pa.) and fluorescence microscopy were used to count live cells, stained green with fluorescein diacetate (Rotman et al., *PNAS USA*, 55, 134 (1966)), and dead cells, stained red with propidium iodide (Pullen et al., *J. Immunol. Methods* 43, 87 (1981)). Viability was calculated by the formula: viability %=(live cells)/(live cells+dead cells))×100%. Each experiment was performed in duplicate and all results represent three or more experiments.

C. Cytokine-mediated Eosinophil Survival and Effects of Topical Anesthetics

As reported by Wallen et al., *J. Immunol.*, 147, 3940 (1991), the responses of eosinophil survival to increasing concentrations of IL-5, IL-3, GM-CSF and IFN-γ were determined. For determination of the effect of lidocaine and other topical anesthetics on cytokine-mediated survival, eosinophils were cultured in the presence of specified cytokine and topical anesthetic concentrations, and viability in the presence of the test anesthetic was compared to viability in cytokine-enriched medium alone. Anesthetics were dissolved in 0.15M NaCl, stored at −20° C., and diluted in medium just before use; thus, 0.15M NaCl was used as a control for each experiment. The effects of the anesthetics and the vehicle control on cytokine-mediated viability were tested. Inhibition of viability was determined by the formula: inhibition %=$(V_{med}-V_{an})/V_{med}\times100\%$, where $V_{med}$= viability in cytokine enriched medium alone and $V_{an}$= viability at the specified anesthetic and cytokine concentrations. $IC_{50}$ is the concentration of anesthetic that produces 50% inhibition of viability. The change in dose-response to cytokine in the presence of varied lidocaine concentrations was tested and the $EC_{50}$ for each lidocaine concentration was calculated. $EC_{50}$ is the IL-5 concentration that produces 50% enhancement of viability; the 50% viability enhancement was determined by subtracting the baseline viability from the maximum viability and dividing the difference by two, or $V_{50}=(V_{max}-V_{min})/2$, where $V_{max}$= viability achieved with optimum cytokine concentration and $V_{min}$=viability in the absence of cytokine and anesthetic. For determination of the time course of the anesthetic effect, medium was supplemented with rhIL-5, 220 fM, or 890 fM, and the effects of anesthetic 1000 nM, 100 nM, or control were tested by comparing viability at 1, 2, and 4 days in the presence or absence of anesthetic.

D. Statistics

All values are expressed at the mean±SEM and represent three or more experiments performed in duplicate. Significance of differences in viability were determined using a one-tailed Student's t-test.

E. Results

Figure 2A:
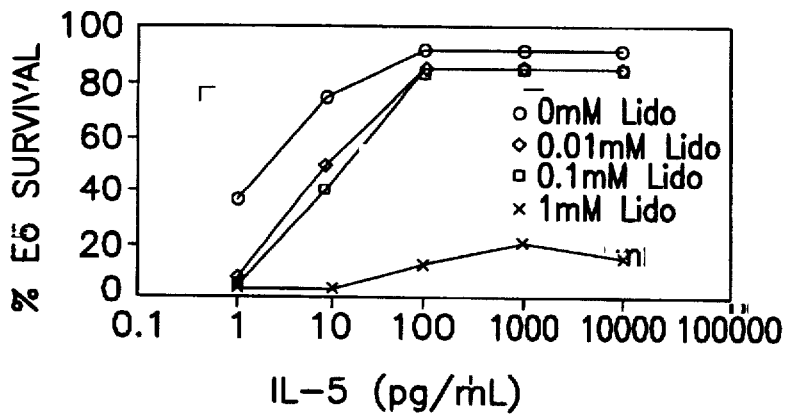
FIGS. 2A–C are graphical depictions of the inhibition of eosinophil survival mediated by cytokines with lidocaine. Purified eosinophils were tested in the eosinophil survival assay for four days and their viability determined by staining with propidium iodide and analysis by FACS.
Figure 2B:
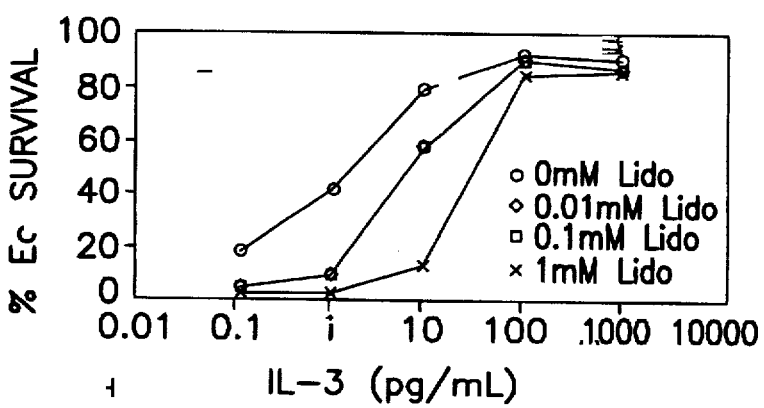
Figure 2C:
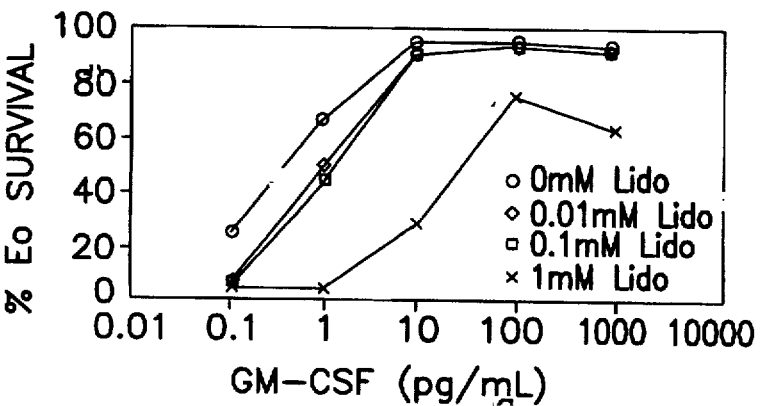

As shown in FIG. 1, when 10 pg/ml IL-5 was used in eosinophil culture, significant inhibition by lidocaine was not seen until day 4 of incubation. Second, as shown in FIGS. 2A–C, the eosinophil survival inhibition produced by lidocaine was largely overcome by high concentrations of IL-3 and GM-CSF, but not by IL-5.

EXAMPLE 2

Inhibition of Eosinophils By Local Anesthetics

To determine whether or not other topical anesthetics, particularly those of the carboxamide (lidocaine) class or benzoate class, also can inhibit eosinophil viability in vitro, the assay of Example 1(C) was carried out. Eosinophils were cultured in the presence of 100 pg/ml II-5 and 1 mM/ml, 0.1 mM/ml and 0.01 mM/ml of lidocaine and nine other topical anesthetics, and viability in the presence of the anesthetic was compared to viability in medium with and without IL-5. The results of this study are summarized on Table 1, below.

TABLE 1

| IL-5 | Local Anesthetic 1 mM/ml | Viable Eosinophils on Day 4 (x ± SD) |
|---|---|---|
| 100 pg/ml | Lidocaine | 10 ± 2 |
| 100 pg/ml | Bupivacaine | 0 ± 0 |
| 100 pg/ml | Chloroprocaine | 54 ± 13 |
| 100 pg/ml | Etidocaine | 0 ± 22 |
| 100 pg/ml | Procaine | 59 ± 22 |
| 100 pg/ml | Tetracaine | 0 ± 0 |
| 100 pg/ml | Benoxinate | 0 ± 0 |
| 100 pg/ml | Proparacaine | 27 ± 8 |
| 100 pg/ml | Dibucaine | 0 ± 0 |
| 100 pg/ml | Dyclonine | 0 ± 0 |
| 100 pg/ml | None | 78 ± 8 |
| 10 pg/ml | None | 69 ± 7 |
| None | None | 22 ± 11 |

As described above, in the eosinophil survival assay, eosinophils are cultured in the absence and the presence of a survival stimulating factor, such as interleukin (IL)-5. In Table 1, eosinophil viability was enhanced over culture medium by addition of 10 or 100 pg/ml of IL-5. For example, the survival of eosinophils in the absence of any survival-enhancing factor was 22% (78% of the eosinophils were dead) at four days. In the presence of IL-5 the survival of eosinophils was increased to 78% by 100 pg/ml of IL-5. In the presence of 100 pg/ml of IL-5, 1 mM of lidocaine inhibited eosinophil survival, such that only 10% of the cells were viable at day 4. Similarly, bupivacaine, etidocaine, tetracaine, benoxinate, dibucaine and dyclonine strikingly inhibited eosinophil survival, suggesting that they were as potent, if not more potent, than lidocaine. In addition, proparacaine also showed weak IL-5 inhibitory activity reducing eosinophil survival from an expected 78% (in the presence of IL-5, 100 pg/ml) to 27%. These data indicate that numerous topical anesthetics have potent effects on eosinophil survival and appear to exhibit a bioactivity which is comparable to that exhibited by lidocaine.

EXAMPLE 3

Treatment of Bronchial Asthma with Lidocaine

Glucocorticoids are believed to be effective to manage bronchial asthma due to their ability to interfere with the cytokine-indicated accumulation and activation of inflammatory cells, including eosinophils. Examples 1–2 indicate that lidocaine and other topical anesthetics are able to mimic the bioactivity of glucocorticoids. Therefore, lidocaine was evaluated for its ability to replace glucocorticoids in the therapy of bronchial asthma.

A. Patient A

Patient A is a woman (age 43) presenting with chronic, severe, glucocorticoid-dependent bronchial asthma. This patient was begun on lidocaine inhalation (2% aqueous lidocaine, 2 ml per nebulization, four times a day) delivered via a deVilbiss nebulizer (Model #5610D). Nebulization of this concentration of lidocaine has not caused side effects other than transient numbness of the oral cavity and of the upper regions of the pharynx and larynx, and this was well tolerated.

Figure 3A:
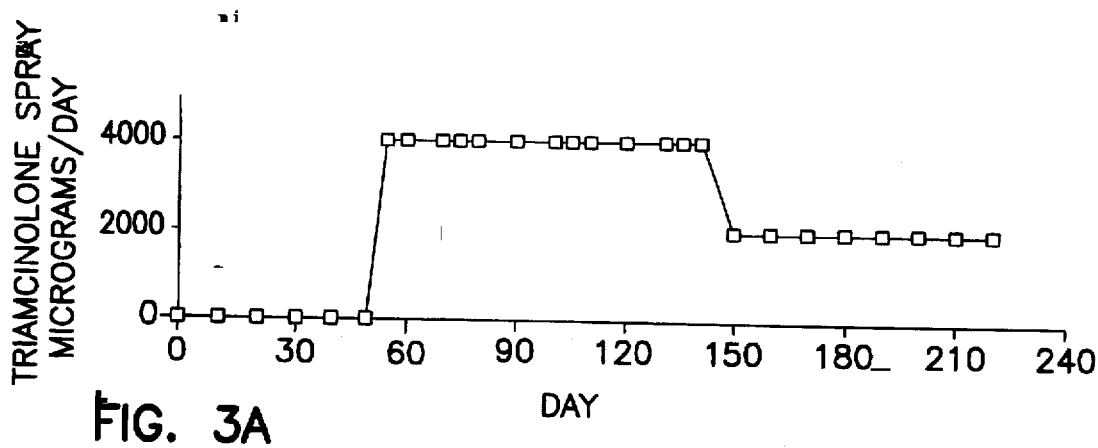
FIGS. 3A–C are graphical depictions of the drug regimen of patient A with respect to inhaled triamcinolone (FIG. 3A), inhaled lidocaine (FIG. 3B) and oral prednisone (FIG. 3C).
Figure 3B:
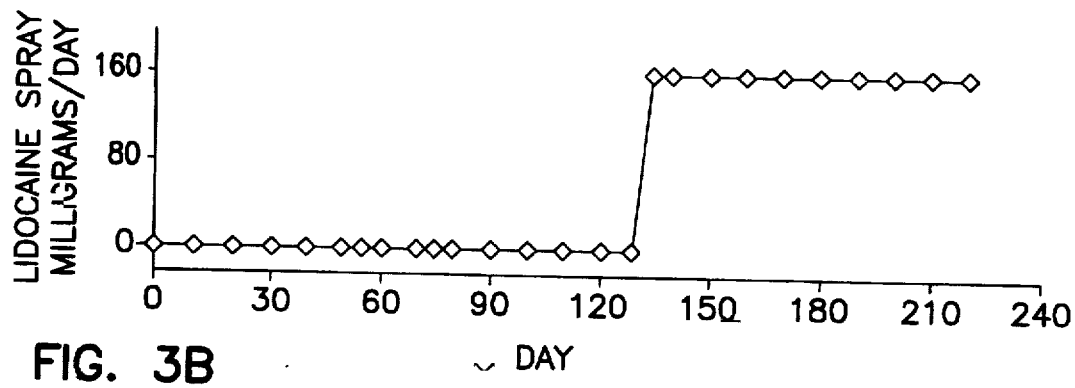
Figure 3C:
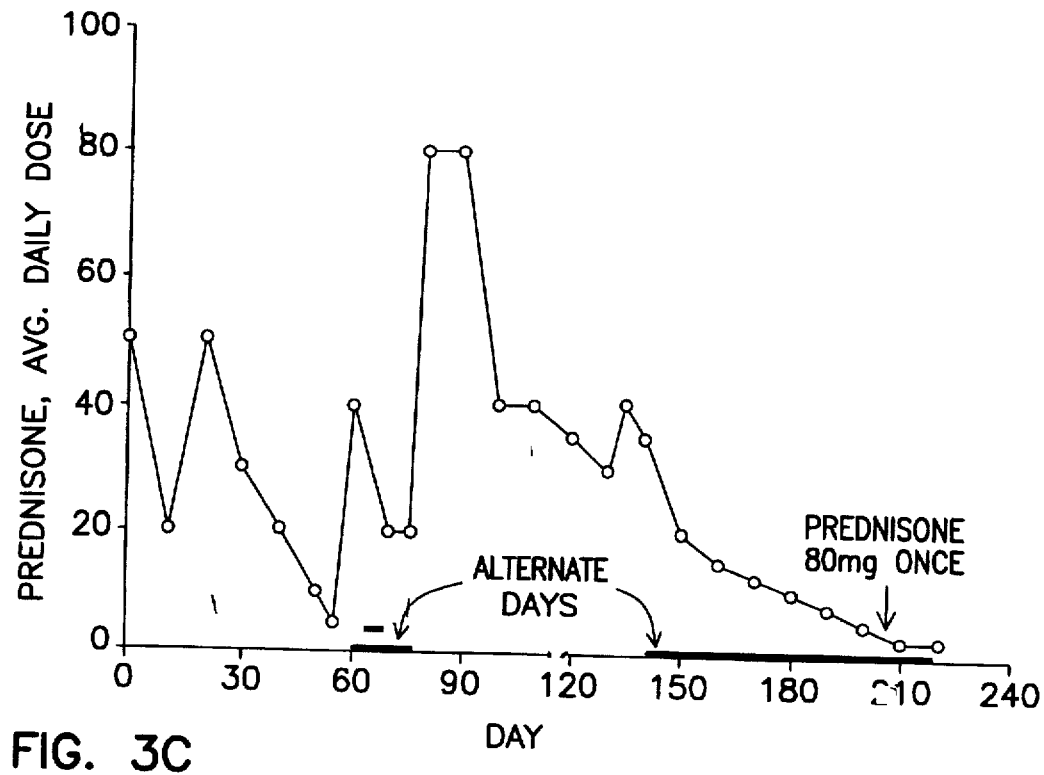

Patient A was begun on lidocaine inhalation in early September 1992, at a time when she was receiving 40 mg of prednisone orally a day, as well as 20 puffs of asthmacort (triamcinolone). Over the preceding four months, the patient had received virtually continuous prednisone therapy. The lowest dose administered was 5 mg daily for a period of a few days in the middle of June 1992. After that reduction in therapy, the patient required a prompt increase in the quantity of glucocorticoids to 40 mg daily and then a taper was done such that she received 40 mg on one day and gradually decreasing doses of prednisone on the alternate day. As shown in FIGS. 3A–C, the patient eventually reached a dose of 20 mg prednisone on one day and no prednisone on the following day, but this regimen was followed by a severe flare of asthma, such that for a period of time in July, she required therapy with 80 mg of prednisone a day.

Initiation of lidocaine therapy in late September was associated with a reduction in the patient's nocturnal cough and with relief of the patient's breathlessness. The prior prednisone therapy, while keeping the asthma under control, did not completely relieve the symptoms, whereas lidocaine therapy was associated with a feeling of well being and virtually complete relief of symptoms. Following initiation of lidocaine therapy, the patient's prednisone was reduced gradually, such that by December 1992, the patient was receiving 5 mg every other day, a dose which she had not been able to achieve other than briefly in June 1992. In mid-November, an exacerbation of asthma occurred following a respiratory tract infection, which was treated by addition to the patient's therapy of one administration of 80 mg of prednisone.

B. Patient B

Figure 4A:
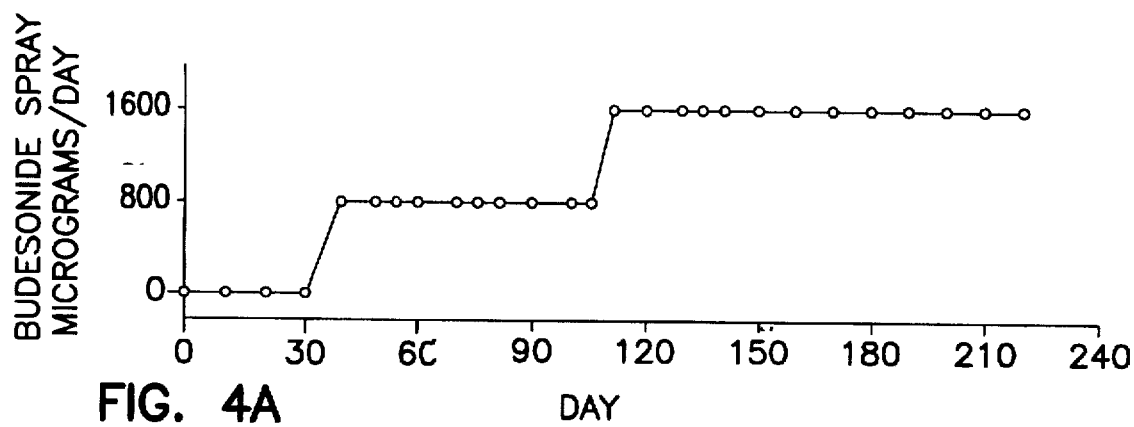
FIGS. 4A–C are graphical depictions of the drug regimen of Patient B with respect to inhaled budesonide (FIG. 4A), inhaled lidocaine (FIG. 4B) and oral prednisone (FIG. 4C).
Figure 4B:
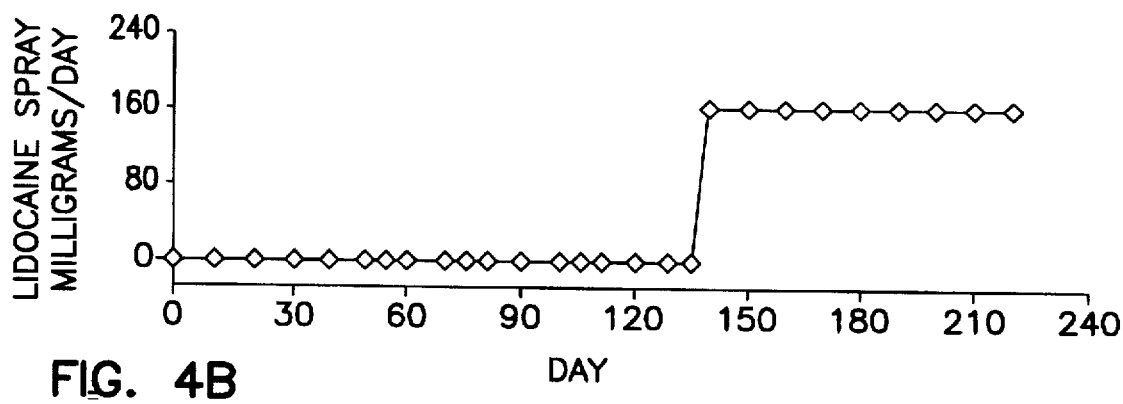
Figure 4C:
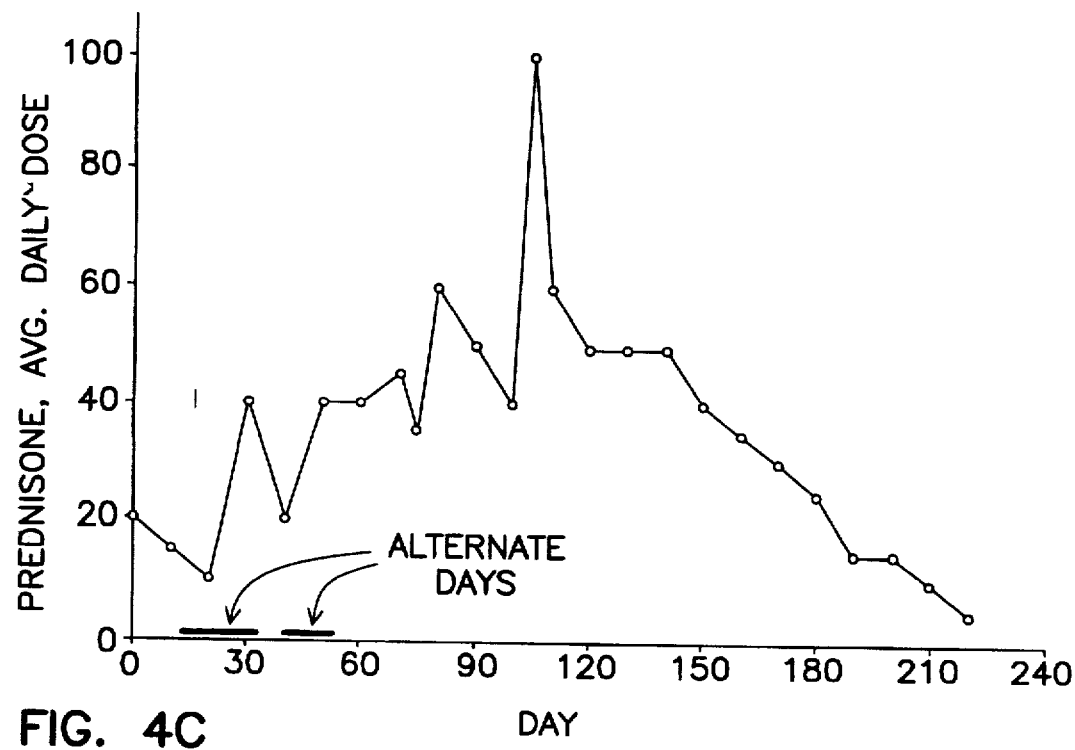

Patient B is a woman (age 34), who was begun on lidocaine therapy around the middle of September 1992, as described in section A, above. As shown by FIGS. 4A–C, she has been able to reduce prednisone therapy from an average of 50 mg daily to a dose of 5 mg daily in early December 1992. This reduction has not been associated with any untoward effects other than those which one anticipates from reduction of glucocorticoids in any patient who has been receiving glucocorticoids for long periods of time. (Glucocorticoid withdrawal causes a characteristic syndrome associated with malaise and muscle aching; both patients A and B have experienced these symptoms).

EXAMPLE 4

The Effects of Lidocaine and Dexamethasone on Isolated Human Eosinophils

The effects of lidocaine and dexamethasone on isolated human eosinophils was determined utilizing an in vitro assay of eosinophil survival. In the below-described experiment, all drugs were purchased from Sigma. Human recombinant IL-5 was generously provided by Shering-Plough Corporation. Lidocaine was resuspended in Hybri-Care media with 10% alpha calf serum and made fresh for each use. Dexamethasone was resuspended in DMSO, and dilutions of the dexamethasone stock solution were made in Hybri-Care® medium supplemented with 10% alpha calf serum. The concentration of DMSO in the dexamethasone solutions added to the eosinophils never exceeded 0.001%.

A. Eosinophil Isolation

Human eosinophils were isolated by layering over Percoll and separation from remaining neutrophils by negative selection using anti-CD16 magnetic beads and MACS column isolation, as previously described by Ide et al., *J. Immunol. Methods*, 168, 187 (1994). The isolated eosinophils were ≥97% pure.

B. Eosinophil-Survival Assay

Isolated eosinophils were incubated in 96-well plates at $2.5 \times 10^5$/mL with varying concentrations of IL-5 plus or minus drugs in a total volume of 200 µl. The eosinophils were incubated for 4 days at $37°$ C. and 5% $CO_2$. To determine percent survival, the total volume of each well was transferred to a separate 12×75 polystyrene tube and stained with 200 µl of a 0.5 mg/mL propidium iodide (PI) solution. The sample was then analyzed on a Becton Dickinson FACScan flow cytometer for PI fluorescence. The percentage of surviving eosinophils is defined as the number of PI-negative eosinophils over the total number of eosinophils gated and analyzed.

C. Results

Figure 5:
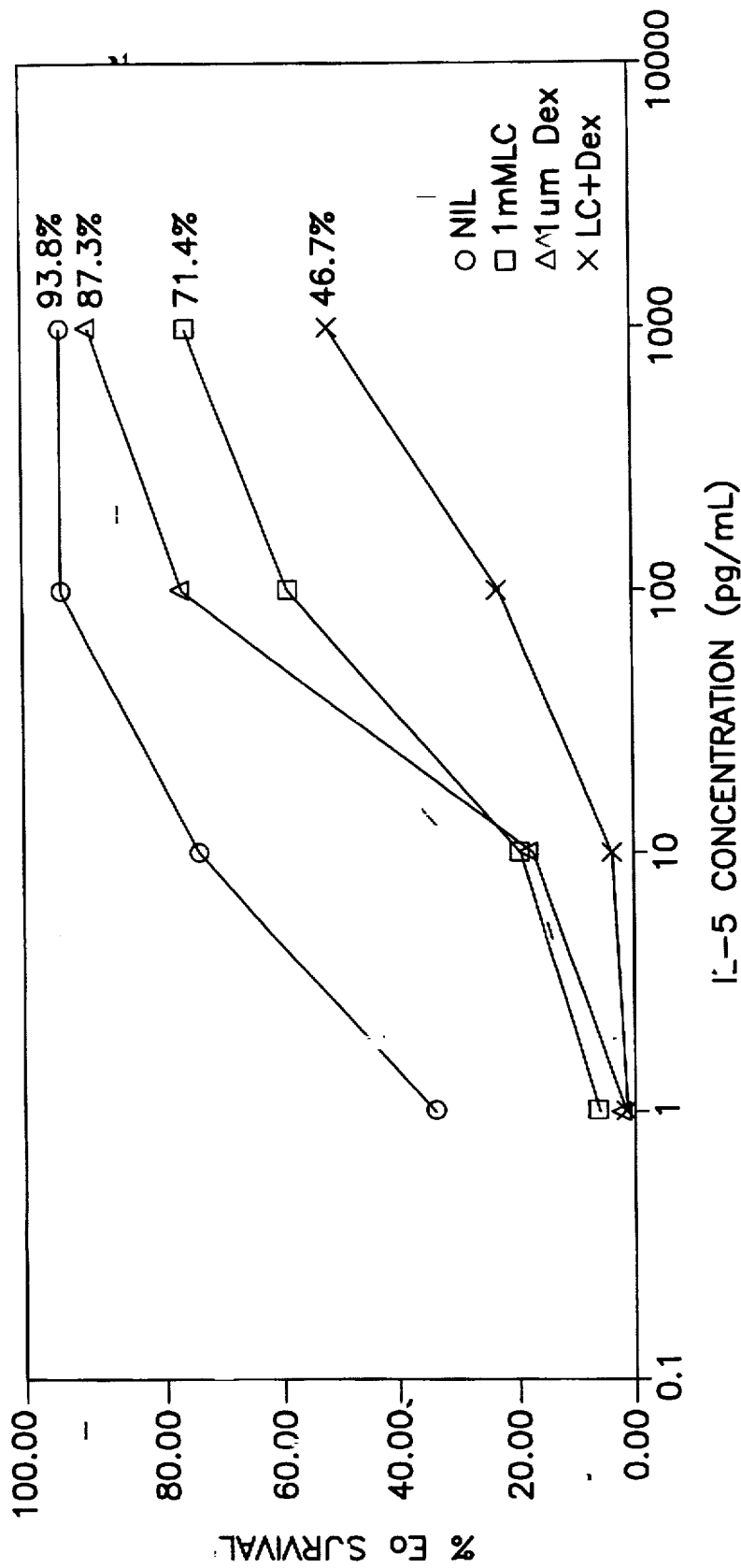
FIG. 5 is a graphical depiction of the effect of lidocaine and dexamethasone on cytokine-mediated eosinophil survival. Isolated eosinophils were incubated in 96-well plates at $2.5 \times 10^5$/mL with varying concentrations of IL-5 plus or minus drugs (LC=lidocaine, Dex=dexamethasone, nil=control) in a total volume of 200 µl Hybri-Care® medium. After four days of culture, percent eosinophil (EO) survival was determined.

As shown in FIG. 5, the synergistic effect of combinations of 1 mM lidocaine (LC) with dexamethasone on eosinophil survival is apparent at 0.1 µM dexamethasone. Lower concentrations of LC may synergize with dexamethasone at lower concentrations of IL-5, but the most striking results were evident at 1000 pg/mL IL-5.

All publications and patents are herein incorporated by reference to the same extent as if each individual publication or patent application was specifically and individually indicated to be incorporated by reference. Specifically, the literature and patents incorporated by reference in the sections on "Topical Anesthetics" and "Glucocorticoids" are incorporated for their teachings of analogs, salts and derivatives of the anesthetics and glucocorticoids specifically disclosed herein, which can also be used in the present invention. It will be apparent to one of ordinary skill in the art that many changes and modifications can be made in the invention without departing from the spirit or scope of the appended claims.

What is claimed is:

1. A method for treating an eosinophil-associated pathology comprising co-administering to a mammal in need of such treatment an amount of a topical anesthetic and an amount of a glucocorticoid, wherein said amounts are effective to counteract at least one of the symptoms of said pathology.

2. The method of claim 1 wherein the mammal is a human.

3. The method of claim 1 wherein the pathology is bronchial asthma, eosinophil-associated intranasal inflammation, inflammation of the paranasal sinuses, allergic rhinitis, eosinophil-associated cutaneous inflammation, eosinophil-associated disorders of the gastrointestinal tract or eosinophil-associated inflammation of the eye.

4. The method of claim 3 wherein the pathology is bronchial asthma.

5. The method of claim 1 wherein the topical anesthetic and the glucocorticoid are administered to the respiratory tract of said human, by spraying or by nebulization.

6. The method of claim 5 wherein the topical anesthetic is administered in combination with a pharmaceutically acceptable liquid vehicle.

7. The method of claim 1 wherein the topical anesthetic is administered at a daily dose of about 0.05–15 mg/kg.

8. The method of claim 1 wherein the topical anesthetic is an N-arylamide aminoalkylbenzoate or a pharmaceutically acceptable salt thereof.

9. The method of claim 1 wherein the topical anesthetic is an aminoalkylbenzoate or a pharmaceutically acceptable salt thereof.

10. The method of claim 8 wherein the topical anesthetic is an N—($C_7$–$C_{22}$) arylamide of an amino-substituted ($C_1$–$C_5$) - carboxylic acid or a pharmaceutically acceptable salt thereof.

11. The method of claim 10 wherein the topical anesthetic is an N-[(mono- or di-($C_1$–$C_4$) alkyl) phenyl]amide of an aliphatic ($C_1$–$C_5$) carboxylic acid, wherein said acid is substituted with (R)($R^1$)N—, wherein R is H or ($C_1$–$C_5$) alkyl and $R^1$ is ($C_1$–$C_5$) alkyl; or a pharmaceutically acceptable salt thereof.

12. The method of claim 11 wherein the topical anesthetic is lidocaine, prilocaine, or etidocaine or a pharmaceutically acceptable salt thereof.

13. The method of claim 12 wherein the topical anesthetic is lidocaine or lidocaine hydrochloride.

14. The method of claim 9 wherein the topical anesthetic is an ester between a carboxylic acid of the general formula:

($R^2$)($R^3$)ArCO$_2$H 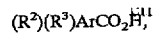

wherein Ar is $C_6H_3$ and each $R^2$ and $R^3$ is H, halo, ($R^5$)(H)N—, $H_2$N—, or ($C_1$–$C_5$)alkyl, and an alcohol of the general formula:

($R^4$)($R^5$)N(X)OH wherein X is a branched- or straight-chain ($C_1$–$C_5$)alkylene; $R^4$ is H or ($C_1$–$C_4$) alkyl, $R^5$ is ($C_1$–$C_4$)alkyl or $R^4$ and $R^5$ taken together with N are a 5- or 6-membered heterocycloaliphatic ring, optionally substituted by ($C_1$–$C_3$) alkyl or comprising an additional ring O— or N— atom, or a pharmaceutically acceptable salt thereof.

15. The method of claim 14 wherein the topical anesthetic is procaine, chloroprocaine, dyclonine, tetracaine, benoxinate, proparacaine, meprylcaine, piperocaine or a pharmaceutically acceptable salt thereof.

16. The method of claim 1 wherein the topical anesthetic is bupivacaine, dibucaine or a pharmaceutically acceptable salt thereof.

17. The method of claim 1 wherein the glucocorticoid is beclomethasone, betamethasone, budesonide, cortisol, cortisone, dexamethasone, flumethasone, fluocinolone, fluocinonide, fluorometholone, flurandrenolide, fluticasone, meprednisone, methylprednisolone, prednisolone, triamcinolone, amcinonide, desonide, desoximetasone, or a pharmaceutically acceptable salt thereof.

18. The method of claim 17 wherein the glucocorticoid is betamethasone, cortisol, cortisone, dexamethasone, meprednisone, methylprednisolone, or prednisolone, or a pharmaceutically acceptable salt thereof.

19. The method of claim 18 wherein the glucocorticoid is dexamethasone, or a pharmaceutically acceptable salt thereof.

20. The method of claim 1 wherein said amounts are co-administered simultaneously.

21. The method of claim 20 wherein a pharmaceutical composition is administered comprising the amount of said topical anesthetic and the amount of said glucocorticoid.

22. The method of claim 20 wherein a first pharmaceutical composition comprising said topical anesthetic in combination with a pharmaceutically acceptable carrier is administered simultaneously with a second pharmaceutical composition comprising said glucocorticoid in combination with a pharmaceutically acceptable carrier.

23. The method of claim 1 wherein said amounts are administered sequentially.

* * * * *